(12) United States Patent
Moroski

(10) Patent No.: US 6,539,248 B1
(45) Date of Patent: *Mar. 25, 2003

(54) DYE MANAGEMENT SYSTEM INCLUDING AN ADMINISTRATION SET WITH AN IN LINE BURETTE

(75) Inventor: Mark T. Moroski, Scranton, PA (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/891,177

(22) Filed: Jul. 10, 1997

Related U.S. Application Data

(63) Continuation of application No. 08/615,579, filed on Mar. 12, 1996, now abandoned, which is a continuation of application No. 08/261,551, filed on Jun. 17, 1994, now abandoned, which is a continuation of application No. 08/091,543, filed on Jul. 14, 1993, now Pat. No. 5,334,170.

(51) Int. Cl.$^7$ .................................................. A61M 5/00
(52) U.S. Cl. ........................ 600/432; 604/183; 604/247; 604/256
(58) Field of Search .......................... 604/80–83, 247, 604/252, 257–258, 183, 262, 403, 407; 137/606; 600/431–435

(56) References Cited

U.S. PATENT DOCUMENTS

| | | | |
|---|---|---|---|
| 2,866,457 A | 12/1958 | Moore ........................ 128/214 |
| 3,001,397 A | 9/1961 | Leonard | |
| 3,021,841 A | 2/1962 | Burke | |
| 3,105,511 A | 10/1963 | Murphy, Jr. | |
| 3,216,418 A | 11/1965 | Scislowicz | |
| 3,230,954 A | 1/1966 | Burgess et al. | |
| 3,276,472 A | 10/1966 | Jinkens et al. | |
| RE26,124 E | 12/1966 | Koehn | |
| 3,664,339 A | 5/1972 | Santomieri | |
| 3,667,464 A | 6/1972 | Alligood, Jr. | |
| 3,756,237 A | 9/1973 | Chittenden et al. | |
| 3,902,489 A | 9/1975 | Carter ........................ 128/214 |
| 4,006,736 A | 2/1977 | Kranys ........................ 128/2 A |
| 4,055,176 A | 10/1977 | Lundquist | |
| 4,105,029 A | 8/1978 | Virag | |
| 4,114,617 A | 9/1978 | Turner et al. | |
| 4,175,558 A | 11/1979 | Hess, III et al. | |
| 4,227,525 A | 10/1980 | Lundquist | |
| 4,237,879 A | 12/1980 | Genese | |
| 4,252,116 A | 2/1981 | Genese et al. | |
| 4,256,104 A | 3/1981 | Muetterties et al. | |
| 4,256,105 A | 3/1981 | Leahey et al. | |
| 4,316,460 A | 2/1982 | Genese et al. | |
| 4,354,492 A | 10/1982 | McPhee | |
| 4,395,260 A | 7/1983 | Todd et al. | |
| 4,396,016 A | 8/1983 | Becker | |
| 4,397,648 A | 8/1983 | Knute | |
| 4,428,383 A | 1/1984 | DeVroom | |
| 4,432,756 A | 2/1984 | Urquhart et al. | |
| 4,468,224 A | * 8/1984 | Enzmann et al. | |
| 4,488,961 A | * 12/1984 | Spencer | |
| 4,525,162 A | 6/1985 | Urquhart et al. | |
| 4,534,757 A | 8/1985 | Geller | |
| 4,540,027 A | * 9/1985 | Forberg | |
| 4,553,964 A | 11/1985 | Sasaki | |
| 4,556,086 A | 12/1985 | Raines | |
| 4,576,592 A | 3/1986 | Danby | |
| 4,601,712 A | 7/1986 | Cole et al. | |
| 4,615,693 A | 10/1986 | Paradis et al. | |
| 4,623,333 A | 11/1986 | Fried | |
| 4,673,397 A | 6/1987 | Lynn et al. | |
| 4,673,400 A | 6/1987 | Martin ........................ 604/283 |
| 4,687,473 A | 8/1987 | Raines | |
| 4,692,144 A | 9/1987 | Carpenter | |
| 4,734,091 A | * 3/1988 | Boyle et al. ........................ 604/54 |
| 4,750,643 A | * 6/1988 | Wortrich ........................ 222/81 |
| 4,858,619 A | 8/1989 | Toth | |
| 4,898,581 A | 2/1990 | Iwatschenko | |
| 4,915,689 A | 4/1990 | Theeuwes | |
| 4,941,875 A | 7/1990 | Brennan ........................ 604/81 |
| 4,946,448 A | * 8/1990 | Richmond | |
| 5,031,654 A | 7/1991 | Kobayashi | |
| 5,032,112 A | 7/1991 | Fairchild ........................ 604/80 |
| 5,045,059 A | 9/1991 | Theeuwes | |
| 5,049,128 A | 9/1991 | Duquette ........................ 604/83 |
| 5,059,173 A | * 10/1991 | Sacco ........................ 604/80 |
| 5,127,904 A | * 7/1992 | Loo et al. | |
| 5,135,489 A | 8/1992 | Jepson et al. | |
| 5,169,393 A | * 12/1992 | Moorehead et al. | |
| 5,215,538 A | 6/1993 | Larkin | |
| 5,236,417 A | 8/1993 | Wallis ........................ 604/82 |
| 5,242,424 A | 9/1993 | Chen | |
| 5,328,463 A | 7/1994 | Barton et al. | |
| 5,356,375 A | 10/1994 | Higley | |
| 5,389,070 A | 2/1995 | Morell | |
| 5,423,751 A | 6/1995 | Harrison et al. | |
| 5,460,603 A | 10/1995 | DeSantis | |
| 5,593,385 A | 1/1997 | Harrison et al. | |

OTHER PUBLICATIONS

Abbott Soluset product line (List Nos. 4214–01; 5831–01; 4205–01; 1726–02; 4965–68; 1876–68; 1882–68; 1717–02; 1864–68; 6412–01; 1991–68; 6647–01; 11744–01; 11398–01; 11745–01), sold prior to Jul. 14, 1992.

* cited by examiner

*Primary Examiner*—Mark Bockelman
(74) *Attorney, Agent, or Firm*—Beth A. Vrioni; Brian R. Woodworth

(57) ABSTRACT

An apparatus wherein the primary dye source is connected to a secondary dye source with sufficient safeguards, including at least one-way check valve and at least one stopcock between the primary dye source and the secondary dye source, to assure a sterile barrier between the primary and secondary dye sources so that less than the total amount of fluid can be transferred from the primary dye source in an amount sufficient to perform a cardiac catheterization procedure.

6 Claims, 3 Drawing Sheets

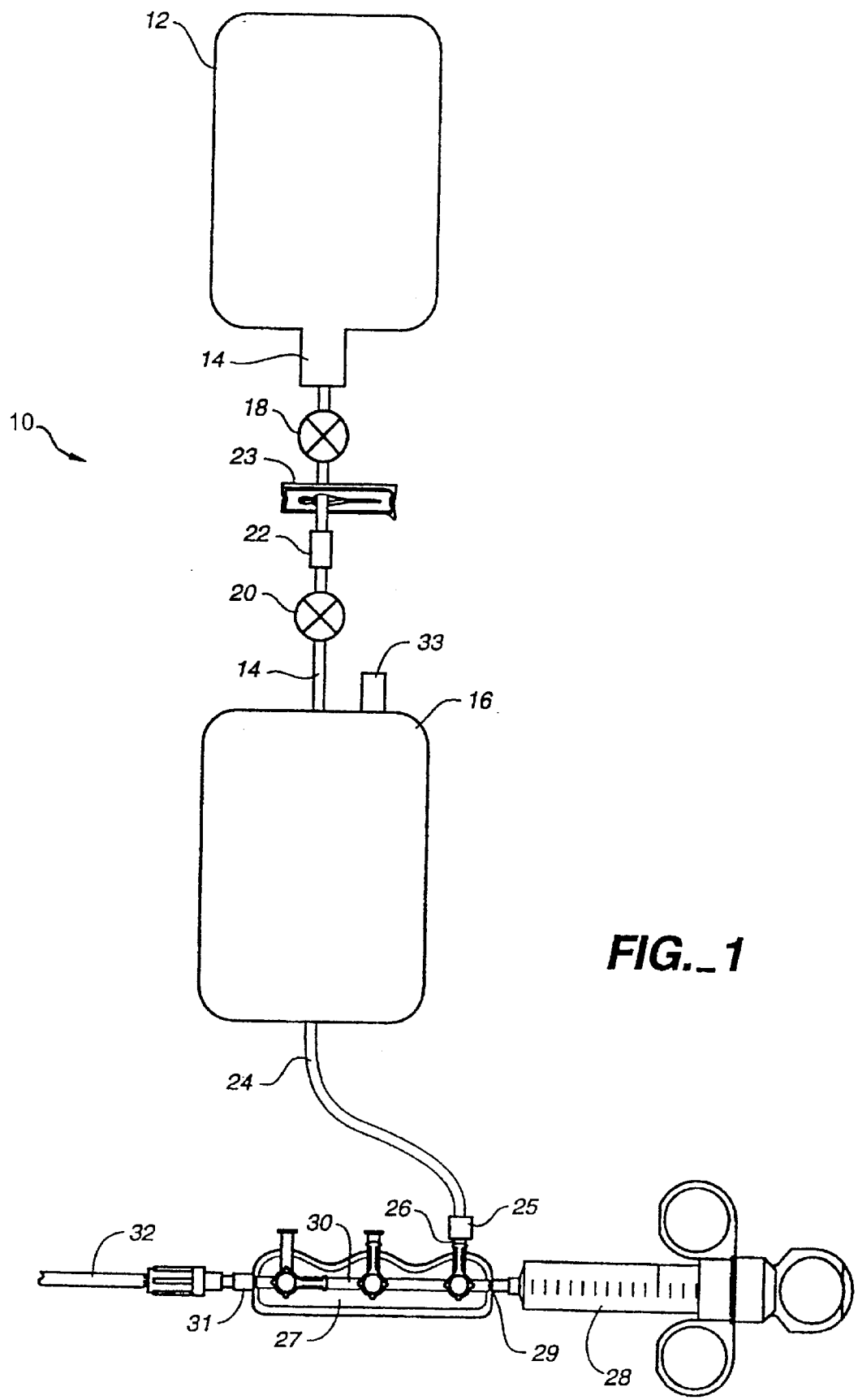
FIG._1

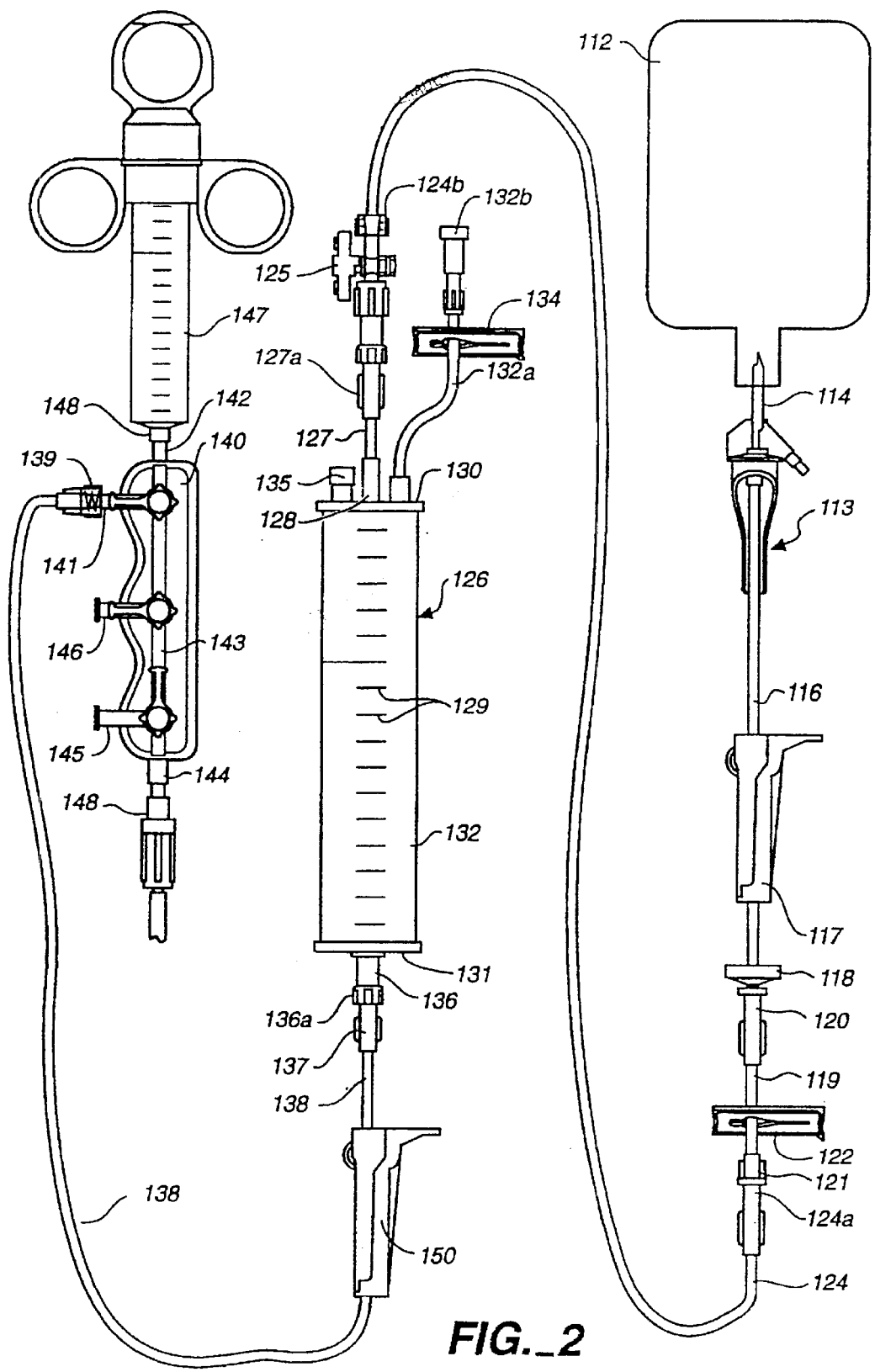
FIG._2

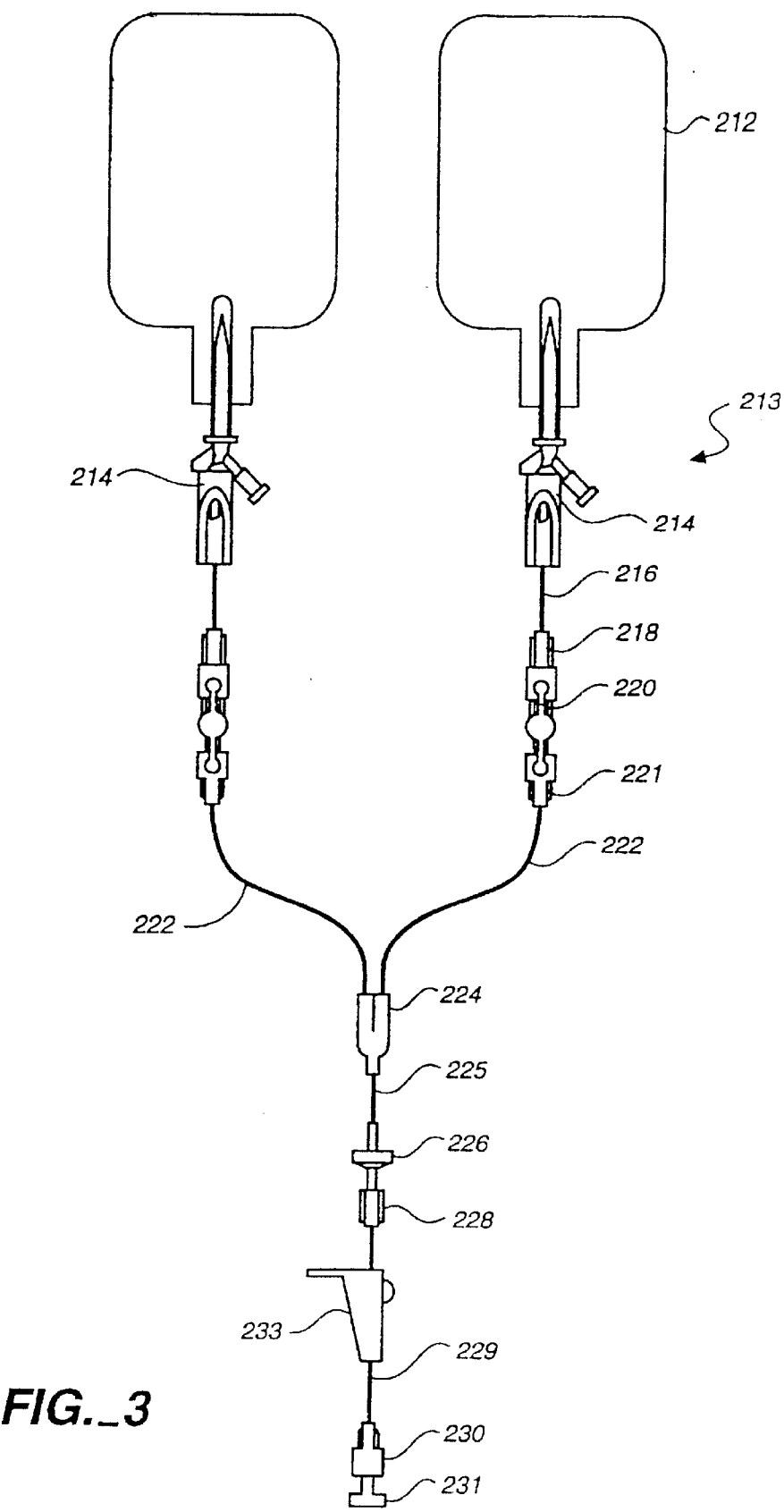
FIG._3

DYE MANAGEMENT SYSTEM INCLUDING AN ADMINISTRATION SET WITH AN IN LINE BURETTE

This application is a continuation of application Ser. No. 08/615,579 filed Mar. 12, 1996, now abandoned, which is a continuation of Ser. No. 08/261,551 filed Jun. 17, 1994, now abandoned, which is a continuation of Ser. No. 08/091,543 filed Jul. 14, 1993, now U.S. Pat. No. 5,334,170.

BACKGROUND OF THE INVENTION

Cardiac catheterization is an invasive procedure which exposes each patient undergoing the procedure and the vasculature of that patient to potential contamination, making sterility a high priority. Because of the risks of cross-contamination, most items used during the catheterization procedure are disposable. Indeed, certain items which it would be desirable to preserve are disposed of in the interest of maintaining patient-to-patient sterility.

For example, non-ionic contrast media or dyes used in a cardiac catheterization procedure are relatively expensive fluids, with costs typically exceeding $1.00 per milliliter (ml). In the current cath lab environment, non-ionic dye media is supplied to the lab in 150 ml containers which is, for the material provided, a standard container. However, a typical catheterization procedure uses anywhere from 80 to 120 mls. At the end of such procedure, the container of non-ionic contrast media is discarded and 30 to 70 mls of contrast media is also discarded with that container, resulting in a loss of 20 to 47 percent of the contents of that container.

In a major cath lab setting where dozens of such procedures are performed every day, the use of non-ionic contrast media over a years time can amount to upwards of one million milliliters of fluid. Thus, an apparatus which could preserve the sterility and integrity of the non-ionic contrast media stored in the container and eliminate waste could produce significant savings in a cath lab. The foregoing example would envision annual savings of $200,000 to $470,000 in a single significant cath lab situation.

Of course, simply saving non-ionic contrast media is not enough. The associated apparatus must maintain the sterile barrier between fluid container and patient and maintain that sterile barrier from patient to patient as well.

SUMMARY OF THE INVENTION

Accordingly, the present invention envisions apparatus wherein the primary dye source, or primary non-ionic contrast media container, is connected to a secondary dye source such as a metered burette, with sufficient safeguards including at least one one-way check valve and at least one stop cock between the primary dye source and the secondary dye source to assure that a sterile barrier exists between the primary dye source and the secondary dye source, so that fluid can be transferred from the primary dye source in an amount sufficient to perform a cardiac catheterization procedure.

Typically, the minimum amount of non-ionic contrast media required to perform a single cardiac catheterization procedure is in the range of 80 to 120 mls. Accordingly, the one-way check valve between the primary dye source and the secondary dye source permits 80 to 120 mls. of non-ionic contrast media to be released into the secondary dye source when the stop cock therebetween is opened. When the transfer of fluid between the primary fluid source and the secondary fluid source is complete, the stop cock is closed to cut of f the fluid transfer and to support the maintenance of a sterile barrier between the primary dye source and the secondary dye source. Should additional fluid be required during the procedure, the stop cock can be reopened to release through the one-way check valve an amount of fluid sufficient to complete the procedure while still maintaining the sterile barrier between the primary dye source and the secondary dye source.

During the cardiac catheterization procedure, fluid flow is from the secondary dye source through a fluid line connected by a catheter to the patient. Before the contrast fluid media is transferred from the secondary dye source to the patient, air bubbles in the contrast media are removed by returning aerated fluid in the line to the secondary dye source and venting the bubbles through a vent-to-air member provided in the secondary dye source, thereby preventing air bubbles from being introduced into the blood stream of the patient. The vent-to-air member prevents a partial vacuum in this retrograde movement application. The vent also discharges air entrapped in the fluid to the atmosphere, as well as replaces fluid with air as such fluid is transferred from the secondary fluid source to the patient.

Further, a sterile barrier is maintained during the cardiac catheterization procedure between the primary dye source and the secondary dye source by the one-way check valve therebetween and, on completion of the catheterization procedure, the secondary dye source can be disconnected from the primary dye source enabling the primary dye source to be connected to a next secondary dye source associated with a second procedure and a second patient.

In an alternate embodiment a pair of vented spikes may each be connected to a primary dye source with proper coupling means connecting the output of each of two primary dye sources to a single connector and then into a single secondary dye source.

The proposed apparatus as described herein eliminates the substantial waste of a relatively expensive non-ionic contrast media, but yet maintains a sterile barrier between primary and secondary dye sources so as to preserve the integrity and the sterility of the catheterization procedure for each patient undergoing the procedure. Further, the apparatus of the present invention enables the development and use of primary fluid source containers of various sizes and configurations to improve the versatility and the convenience of such containers, as well as to further minimize waste in the catheterization procedure.

A BRIEF DESCRIPTION OF THE DRAWINGS

The above described apparatus will be better understood when the drawings briefly described below are considered with the detailed description which follows.

FIG. 1 is a schematic diagram of the dye management system of the present invention showing a primary dye source, a secondary dye source and the connecting apparatus therebetween to preserve the sterility of the connection therebetween;

FIG. 2 is a detailed drawing of a preferred embodiment of the system displayed schematically in FIG. 1; and FIG. 3 is an alternate embodiment of the system of FIG. 2 wherein each of a pair of vented spikes may be connected to a respective primary dye source, to be connected to the described tubing and then to a single secondary dye source.

DETAILED DESCRIPTION

The dye management system 10 of the present invention is best seen in FIG. 1 wherein the system 10 is shown in schematic form. The primary dye source 12 comprises the original container for the non-ionic contrast media used in a catheterization procedure. The primary dye source 12 is connected to a secondary dye source 16 by tubing 14. In the preferred embodiment, the secondary dye source 16 is an in-line metered burette. Provided in the connecting tubing 14 between primary dye source 12 and secondary dye source 16 is a one-way check valve 18 and a stop cock 20. Also provided is a disconnect 22, such as a luer lock connector, between the stop cock 20 and the one-way check valve 18. The disconnect 22 enables separation of the secondary dye source 16 from the primary dye source 12 without compromising the sterile barrier created between the primary dye source 12 and the secondary dye source 16 by the one-way check valve 18. A slide clamp 23 is interposed between the primary fluid source 12 and the disconnect 22.

Extending from the bottom of the burette 16 is a fluid line 24 which is connected by a suitable luer lock fitting 25 to a fluid input port 26 of a multi-port manifold 27. Syringe 28 is connected to a syringe port 29 of the manifold 27. A throughport line 30 of the manifold 27 connects the syringe port 29 to a catheter port 31 disposed on the manifold 27 opposite the syringe port 29. Catheter 32 connects to the port 31 at a proximal end thereof and to the patient (not shown) at a distal end thereof.

The fluid input port 26 and the syringe port 29 are then opened to enable the syringe 28 to retract and draw contrast media from the burette 16 into the syringe. Fluid line 24 can be debubbled by depressing the syringe 28 with the fluid input port 26 and the syringe port 29 open to return air bubbles through the fluid line 24 and back into the in-line burette 16. A vent 33 enables the burette 16 to vent air returned thereto via fluid line 24. Once the fluid line 24, the manifold 27 and the syringe 28 have been primed to remove all air therefrom, the syringe is filled with sufficient contrast media (10–12 mls) to conduct a first phase of the cardiac catheterization procedure. The vent 33 of secondary dye source 16 also enables the user to replace the fluid being transferred from the in-line burette 16 to the patient with air, thus to prevent a partial vacuum from occurring in the fluid line 14 between the primary dye source and the secondary dye source. The cardiac catheterization procedure is multiple injection procedure, wherein the end position of the catheter in the patient's heart is changed prior to each fluid injection of 10–12 ml, to enable multiple pictures of various portions of the patient's cardiovascular system during the cardiac catheterization procedure.

The preferred embodiment of the dye management system 10 of the present invention is shown in FIG. 2. In the preferred embodiment of FIG. 2 an administration set 113 connects the primary dye source 112 to a secondary dye source, an in-line burette 126. Administration set 113 has provided at a proximal end thereof a vented spike. 114. In the preferred embodiment primary dye source 112 comprises a standard 150 milliliter (ml) container of non-ionic contrast media. In alternative configurations permitted by the dye management system of the present invention, the standard 150 ml glass container can be replaced by a 100 ml glass container, or by plastic bags containing the dye, such bags ranging in size from 100 to 200 mls or larger. Container sizes in excess of 150 mls particularly emphasize the advantages of the dye management system of the present invention, since the present system not only effects direct savings of dye in the cath lab, but also enables the manufacturer to reduce packaging costs by enabling them to package and sell dye in the larger containers.

The primary dye source 112 has connected thereto the vented spike 114 which connects a fluid line 116 to the primary dye source 112. A one-way check valve 118 is connected at its proximal end to the fluid line 116 And connected to a second fixed tubing section 119 at a distal end thereof. An adjustable clamp 117, for example, a slide or roller clamp, is provided on the fluid line 116 between the spike 114 and the one-way check valve 118.

The tubing section 119 includes at a first end a female luer lock connector 120 bonded to the distal end of one-way check valve 118 and at an opposite end a male luer lock connector 121. A slide clamp 122 is received on the fixed tubing section 119. A third removable tubing sect ion 124 having respective female and male luer lock connectors 124a, 124b at opposite ends is connected at one end to fixed tubing section 119 and at an opposite end to a proximal end of a stop cock 125.

The stop cock 125 is connected to burette tubing 127 of the in-line burette 126 at the proximal end thereof. The proximal end of burette tubing 127 includes a female luer lock connector 127a which is connected to the distal end of the stop cock 125. The distal end of burette connector tubing 127 is fixedly connected to the burette 126 at burette input tube 128 in an upper wall 130 of the burette.

The in-line burette 126 is a cylindrical member having a top wall 130, a bottom wall 131 and cylinder 132 therebetween, with metering indicia 129 provided on the cylinder 132 to enable the user to easily measure the amount of non-ionic contrast media transferred from the primary fluid source 112 through administration set 113 into the burette 126.

On the upper wall 130 of the burette 126 is also provided a vent-to-air member 132 which includes a tubing section 132a and a filter element 132b. Mounted on tubing section 132a is a slide clamp 134. An injection port 135 is also provided on the upper wall 130 of the burette 126.

On the bottom wall 131 of the burette 126 is provided a central outlet defined by a short section of PC tubing 136 which is molded in place. A male luer lock connector 136a, provided at the distal end of the tubing 136 engages female connector 137 which extends from a proximal end of burette distal tubing 138 which extends between the lower end of the burette 126 and a manifold 140.

Fluid line 138 carries on its distal end a male luer lock connector 139 which is connected to a fluid input port 141 of a multi-port manifold 140. The manifold 140 includes a syringe port 142, a through-put line 143 and a catheter port 144. The manifold 140 also includes input ports 145 and 146, which need not be discussed in detail here.

A manual syringe 147 is connected to the syringe port 142 at one end of through-put line 143. A catheter 148 is connected to catheter port 144, which is at the opposite end of through-put line 143. Conventional manifold plumbing enables opening and closing of the above-described manifold ports in the sequence described in greater detail below.

An adjustable roller clamp 150 is provided on fluid line 138 between in-line burette 126 and the manifold 140.

In operation, the administration set 113 functions as follows.

To enable fluid flow from the primary dye source or primary container 112 to the secondary dye source or in line burette 126, a first adjustable roller clamp 117 mounted on fluid line 116 is opened and the slide clamp 122 on the fixed tubing section 119 is also opened. Then the stop cock 125 is opened to admit fluid through the tubing section 116, the fixed tubing section 119, the removable tubing section 124 and the burette tubing 127 to admit the non-ionic contrast media into the burette 126. Fluid flow through the administration set 113 is continued until non-ionic contrast fluid media is transferred into the in-line burette 126 in an amount sufficient to conduct a cardiac catheterization procedure (80 to 120 mls).

At this point, the adjustable clamp on tubing section 116 is closed to prevent further flow of fluid from the primary dye source 112 into the in-line burette 126. Next the slide clamp 122 carried on the fixed tubing section 119 is closed and then the stop cock 125 is closed to prevent further non-ionic contrast media from being transferred from the primary dye source 112 to the secondary dye source or in-line burette 126. During the fluid transfer procedure, the user can readily measure the amount of fluid being transferred to the in-line burette 126 through use of the metering indicia 129 provided on the in-line burette.

During the loading of the in-line burette from the primary fluid source 112, vented spike 114 admits air to the primary fluid source 112 to prevent a partial vacuum from occurring in the primary fluid source by replacing fluid removed therefrom with air taken in through the vented spike 114. With clamps 117, 122 and the stop cock 125 closed, no further fluid can be passed into the in-line burette 126 and the system is ready to dispense the fluid from the burette to the catheter 148 attached to the patient.

To pass fluid from the in-line burette 126 to the patient, the adjustable roller clamp 150, fluid input port 141, and rotator port 142 are opened to enable fluid to travel from the in-line burette 126 through set tubing 138 through fluid input port 141 and syringe port 142 of manifold 140. Fluid is drawn from the in-line burette 126 by retracting the syringe 147 connected to the syringe port 142 of the manifold 140. Fluid flow is from the in-line burette 126 through tubing 138 through the fluid input port 141 through syringe port 142 and into the syringe 147.

Set tubing 138 is primed to enable removal of air from tubing 138 prior to fluid transfer from in-line burette 126 to the manifold 140. With the fluid input port 141, the syringe port 142 open, fluid can be returned through set tubing 138 and into burette 126 by extending the syringe to the closed position to return air-in-line to the burette 126 which vents such air through the vent-to-air member 132.

Once the fluid line 138, the manifold 140 and the syringe 147 have been primed to remove all air therefrom, the syringe is filled with sufficient contrast media (10–12 ml) to conduct a first phase of the cardiac catheterization procedure. The fluid input port 141 may be closed to prevent further ingress of contrast media to the manifold 140. With the fluid input port 141 closed, through-put line 143 is opened thereby enabling fluid flow from the syringe 147, through the manifold 140, through the catheter 148 and into the patient. The cardiac catheterization procedure is a multiple injection procedure, wherein the end position of the catheter in the patient's heart is changed prior to each fluid injection of 10–12 ml, to enable multiple pictures of various portions of the patient's cardiovascular system during the cardiac catheterization procedure. During the fluid transfer from the in-line burette 126 to the catheter 148 connected to the patient, the slide clamp 134 is opened to enable the vent-to-air member 132 to admit air to the in-line burette 126 while fluid is drawn therefrom to assure that no partial vacuum is created either in the inline burette or in the fluid line between the primary dye source and the secondary dye source during the period of fluid withdrawal.

The slide clamp 134 is also engaged if the catheterization procedure is interrupted while contrast media remains in the burette to prevent fluid flow out of the burette 126 through the vent 132 during the interruption in such procedure.

When the procedure is complete, slide clamp 122 is closed, and the burette assembly distal of fixed tubing section 119 is separated from the administration set 113. The separated assembly remains intact for disposal and includes removable tubing section 124, stop cock 125, burette tubing 127, in-line burette 126, set tubing 138, the manifold 140 and the syringe 147. A sterile vented cover 231 (see FIG. 3A) is then placed over the male luer lock connector 121 of the fixed tubing section 119 to maintain the sterility of the primary dye source 112 until a second new sterile burette assembly which would include the removable tubing section 124 and all associated disposable components as enumerated above can be attached thereto to enable the primary dye source 112 to be used in a second procedure with another patient.

Alternative Embodiment

An alternative embodiment of the present invention is shown in FIG. 3, wherein a pair of primary fluid sources 212 each receive a vented spike 214 of an administration set 213 provided at the proximal end of tubing 216. At the distal end of each tubing set 216 is provided female adapter 218, which connects each tubing set 216 to a one-way stop cock 220 to which is fixedly connected to a tubing section 222 by means of a male luer lock connector 221.

At respective distal ends thereof, each tubing section 222 is received in the proximal end of a two way connector 224. Tubing section 225 connects the distal end of the connector 224 to the proximal end of a one-way check valve 226. A female luer lock adapter 228 is received into the distal end of the one-way check valve 226 to connect tubing section 229 to the check valve 226 at one end.

A sterile vented cover 231, shown in greater detail in FIG. 3A, is connected to male luer lock connector 231 to provide a sterile barrier for administration set 213 prior to use. After the cover 231 is removed, male luer lock connector 230 is joined to female luer lock connector 124a of removable tubing section 124 of an in-line burette 126 and related assembly as set forth above.

In all respects the connections to administration set 213 from the removable tubing section 124 to the in-line burette 126 and thereafter to the patient are the same as the connections distal to tubing section 119 shown in FIG. 2 and need not be discussed in detail here.

To deliver non-ionic contrast media or any other fluid to the patient with the apparatus of FIG. 3, fluid flow from one of primary fluid sources 212 is initiated by opening one of the one-way stop cocks 220 to admit fluid through respective lines 216 and 221, to the connector 224. The one-way check valve 226 carries fluid through lines 225 and 229 to the fluid line 124, stop cock 125, burette line 127 and into the in-line metered burette 126.

While the apparatus described herein constitutes a preferred embodiment of the invention, it is to be understood that the invention is not limited to this precise apparatus and that changes may be made without departing from the scope of the invention, which is defined in the appended claims.

I claim:

1. A fluid management system for delivering a fluid from a plurality of primary fluid containers to a patient, said system comprising:
    a secondary fluid container;
    a plurality of fluid flow input lines, each of said plurality of primary fluid flow input lines having a distal end portion in fluid communication with said secondary fluid container and having a proximal end portion constructed to be fluidly connected to at least one of a plurality of primary fluid containers, each of said plurality of fluid flow input lines defining a fluid flow path therethrough;

a connector in fluid communication with said distal end portion of each of said plurality of fluid flow input lines, said connector defining a secondary fluid container input line fluidly connected to each of said plurality of fluid flow input lines, said secondary fluid container input line having a proximal end portion and a distal end portion, said proximal end portion of said secondary fluid container line in fluid communication with said plurality of fluid flow input lines, said distal end portion of said secondary fluid container input line constructed to be fluidly connected to said secondary fluid container;

a fluid flow control means for selectively interrupting fluid flow disposed in said secondary fluid container input line intermediate said proximal end portion and said distal end portion of said secondary fluid container input line;

a one-way fluid flow control means for preventing fluid flow from said secondary fluid container to the plurality of primary fluid containers disposed in said secondary fluid container input line intermediate said proximal end portion and said distal end portion of said secondary fluid container input line; and a disconnect means for selective disconnection of said secondary fluid container from the plurality of primary fluid containers mounted on said secondary fluid container input line intermediate said proximal end portion of said secondary fluid container input line and said distal end portion of said secondary fluid container input line.

2. A fluid management system in accordance with claim 1, wherein each of said plurality of fluid flow input lines includes a vented spike at said proximal end portion thereof, each of said vented spikes defining an open fluid flow path from at least one of the plurality of primary fluid containers to at least one of said fluid flow input lines.

3. A fluid management system in accordance with claim 1, wherein said secondary fluid container comprises a burette having a top wall, a bottom wall and a cylinder disposed between said top wall and said bottom wall, said top wall defining a fluid input opening therethrough and said bottom wall defining a fluid output opening therethrough, said cylinder having metering indicia thereon, said distal end portion of said secondary fluid container input line fluidly connected to said burette through said fluid input opening defined through said top wall, and wherein said system further comprises a fluid infusion line fluidly connected to said burette through said fluid output opening defined through said bottom wall.

4. A method of transferring a fluid from a primary fluid container to a patient, said method comprising:

providing a secondary fluid container;

providing a fluid flow input line having a proximal end portion and a distal end portion, said proximal end portion constructed to be fluidly connected to a primary fluid container and said distal end portion fluidly connected to said secondary fluid container;

fluidly connecting said proximal end portion of said fluid flow input line to a primary fluid container;

providing a fluid flow control means for interrupting fluid flow through said fluid flow input line in said fluid flow input line;

providing a one-way fluid flow control means for preventing fluid return from said secondary fluid container to the primary fluid container in said fluid flow input line;

providing an infusion line for delivering fluid from said secondary container to a patient, said infusion line having a proximal end portion constructed to be fluidly connected to said secondary container;

connecting said proximal end portion of said infusion line to said secondary fluid container;

providing a multi-port manifold for delivering fluid from said infusion line to the patient, said multi-port manifold having a fluid input port, a syringe port, a catheter port, and a throughput line interconnected between said fluid input, syringe, and catheter ports;

fluidly connecting a distal end portion of said infusion line to the multi-port manifold;

fluidly connecting the catheter port to the patient;

transferring fluid from the primary fluid container to said secondary container;

drawing fluid into the syringe from the secondary container through said infusion line; and transferring fluid from the syringe to the patient through the throughput line and the catheter port.

5. A fluid management system for delivering a fluid from a primary fluid container to a patient, said system comprising:

a secondary fluid container;

a fluid flow input line having a distal end portion fluidly connected to said secondary fluid container and having a proximal end portion constructed to be fluidly connected to a primary fluid container, said fluid flow input line defining a fluid flow path therethrough from said proximal end portion to said distal end portion;

a fluid flow control means for selectively interrupting fluid flow through said fluid flow input line disposed in said fluid flow input line intermediate said proximal end portion and said distal end portion of said fluid flow input line;

a one-way fluid flow control means for preventing fluid flow from said secondary fluid container to the primary fluid container disposed in said fluid flow input line intermediate said proximal end portion and said distal end portion of said fluid flow input line;

a disconnect means for selective disconnection of said secondary fluid container from the primary fluid container mounted on said fluid flow input line intermediate said proximal end portion of said fluid flow input line and said fluid flow control member and intermediate said proximal end portion of said fluid flow input line and said one-way fluid flow control device; and a cap constructed to engage said proximal end portion of said fluid flow input line after disconnection of said disconnect member.

6. A fluid management system for delivering fluid from a plurality of primary fluid containers to a patient, said system comprising:

a secondary fluid container;

a plurality of fluid flow input lines, each of said plurality of primary fluid flow input lines having a distal end portion in fluid communication with said secondary fluid container and having a proximal end portion constructed to be fluidly connected to at least one of a plurality of primary fluid containers, each of said plurality of fluid flow input lines defining a fluid flow path therethrough;

a connector in fluid communication with said distal end portion of each of said plurality of fluid flow input lines, said connector defining a secondary fluid container input line fluidly connected to each of said plurality of fluid flow input lines, said secondary fluid container input line having a proximal end portion and a distal end portion, said proximal end portion of said secondary fluid container fluidly connected to said connector, said distal end portion of said secondary fluid container input line constructed to be fluidly connected to said secondary fluid container;

a fluid flow control means for selectively interrupting fluid flow disposed in said secondary fluid container input line intermediate said proximal end portion and said distal end portion of said secondary fluid container input line;

a one-way fluid flow control means for preventing fluid flow from said secondary fluid container to the plurality of primary fluid containers disposed in said secondary fluid container input line intermediate said proximal end portion and said distal end portion of said secondary fluid container input; and a disconnect means for selective disconnection of said secondary fluid container from the plurality of primary fluid containers mounted on said secondary fluid container input line intermediate said proximal end portion of said secondary fluid container input line and said fluid flow control member and intermediate said proximal end portion of said secondary fluid container input line and said one-way fluid flow control device; and a cap constructed to engage at least one of said proximal end portions of said plurality of fluid flow input lines after disconnection of said disconnect member.

\* \* \* \* \*